US011071495B2

(12) United States Patent
Okada et al.

(10) Patent No.: US 11,071,495 B2
(45) Date of Patent: Jul. 27, 2021

(54) MOVEMENT EVALUATION SYSTEM AND METHOD

(71) Applicant: Hitachi, Ltd., Tokyo (JP)

(72) Inventors: Mitsuhiro Okada, Tokyo (JP);
Takehiro Niikura, Tokyo (JP);
Katsuyuki Nakamura, Tokyo (JP);
Takuto Sato, Tokyo (JP); Hiroki Ohashi, Tokyo (JP); Sheraz Ahmed, Kaiserslautern (DE); Mohammad Osamh Adel Al-Naser, Kaiserslautern (DE)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 16/681,921

(22) Filed: Nov. 13, 2019

(65) Prior Publication Data

US 2020/0253541 A1 Aug. 13, 2020

(30) Foreign Application Priority Data

Feb. 7, 2019 (JP) .............................. JP2019-020447

(51) Int. Cl.
*G08B 21/02* (2006.01)
*A61B 5/11* (2006.01)
*A61B 5/00* (2006.01)
*G06N 3/04* (2006.01)

(52) U.S. Cl.
CPC ............ *A61B 5/486* (2013.01); *A61B 5/1116* (2013.01); *A61B 5/1124* (2013.01); *G06N 3/0454* (2013.01); *G08B 21/02* (2013.01); *A61B 2503/20* (2013.01)

(58) Field of Classification Search
None
See application file for complete search history.

(56) References Cited

U.S. PATENT DOCUMENTS

| 7,475,073 | B2 * | 1/2009 | Leymann ............... G06Q 10/10 |
| 9,262,674 | B2 * | 2/2016 | Kawaguchi ............... G06T 7/77 |
| 9,280,716 | B2 * | 3/2016 | Yamaguchi ........... G06F 3/0425 |
| 10,426,682 | B2 * | 10/2019 | Tsusaka ............... A61G 7/1017 |
| 10,470,667 | B2 * | 11/2019 | Corley ................. A61B 5/0205 |
| 10,478,126 | B2 * | 11/2019 | Najafi .................. A61B 5/0816 |
| 10,682,097 | B2 * | 6/2020 | Bruno ................ G08B 21/0423 |
| 10,755,817 | B2 * | 8/2020 | Mariottini .............. G16H 50/20 |
| 10,832,058 | B2 * | 11/2020 | Guan ................. G06K 9/00744 |
| 10,842,415 | B1 * | 11/2020 | Jagannathan ...... A63B 24/0062 |
| 10,853,636 | B2 * | 12/2020 | Yu ....................... G06K 9/00342 |

(Continued)

FOREIGN PATENT DOCUMENTS

| JP | 2018-25932 A | 2/2018 |
| JP | 2018-55611 A | 4/2018 |

*Primary Examiner* — Muhammad Adnan
(74) *Attorney, Agent, or Firm* — Mattingly & Malur, PC

(57) ABSTRACT

The present invention is provided to notify a person who makes a movement of a part to be improved in the movement. A movement evaluation system includes: a proficiency degree estimating unit generating a proficiency degree score on the basis of movement data obtained by detecting a movement of a user; an improvement point extracting unit specifying a part of the movement of the user as an improvement point on the basis of the movement data; and an information generating unit generating suggestion information to be presented to the user, on the basis of the improvement point.

11 Claims, 13 Drawing Sheets

(56) References Cited

U.S. PATENT DOCUMENTS

| | | | | |
|---|---|---|---|---|
| 10,898,999 | B1* | 1/2021 | Cohen | G06K 9/00362 |
| 2011/0295655 | A1* | 12/2011 | Tsuji | G06Q 10/0639 |
| | | | | 705/7.38 |
| 2013/0171601 | A1* | 7/2013 | Yuasa | A61B 5/744 |
| | | | | 434/258 |
| 2015/0351655 | A1* | 12/2015 | Coleman | G16H 50/20 |
| | | | | 600/301 |
| 2016/0070958 | A1* | 3/2016 | Whelan | A61B 5/1123 |
| | | | | 382/107 |
| 2016/0081594 | A1* | 3/2016 | Gaddipati | A61B 5/1117 |
| | | | | 600/595 |
| 2017/0061817 | A1* | 3/2017 | Mettler May | A61B 5/486 |
| 2018/0046150 | A1* | 2/2018 | Ooba | G05B 13/027 |
| 2018/0089976 | A1* | 3/2018 | Yarlagadda | G06Q 10/063118 |
| 2019/0206270 | A1* | 7/2019 | Agnew | G06Q 10/101 |
| 2020/0074380 | A1* | 3/2020 | Mori | G09B 19/003 |

* cited by examiner

MOVEMENT EVALUATION SYSTEM AND METHOD

The present application claims priority from Japanese application JP 2019-020447, filed on Feb. 7, 2019, the contents of which is hereby incorporated by reference into this application.

BACKGROUND

The present invention relates to a technique of evaluating the quality of a movement of a human, for example, the proficiency degree of a work.

For safety and efficiency of a work, there is a demand to know, for example, a worker working in a bad posture and urge the worker to notice the posture.

Japanese Unexamined Patent Application Publication No. 2018-55611 discloses a device having an obtaining unit obtaining biological information measured from a worker, a storage unit for storing the biological information according to proficiency degree of the worker by proficiency degree, a determining unit comparing a feature amount of the biological information obtained at the time of a work with a feature amount of the biological information by proficiency degree in the storage unit and, on the basis of a result of the comparison, determining the proficiency degree to which the biological information obtained corresponds, and a decision unit deciding a control amount of a driving unit on the basis of the determined proficiency degree.

Japanese Unexamined Patent Application Publication No. 2018-25932 discloses a work management system including a sensor obtaining data of a worker and a cell control device coupled to the sensor. The cell control device includes: a sensor managing unit managing information from the sensor; a worker observing unit monitoring at least one of a movement amount of the worker and a state amount; a learning unit learning at least one of fatigue degree, proficiency degree, and interest degree of the worker; and a notifying/managing unit receiving a state notification request from a higher-level managing unit, transmitting state information including at least one of the fatigue degree, proficiency degree, and interest degree of the worker, receiving a work change notification, transmitting the work change notification to the worker or receiving a state notification request from the worker, and transmitting state information including at least one of the fatigue degree, proficiency degree, and interest degree of the worker to the worker.

In the conventional techniques, however, a person who makes movement cannot know which part in the movement of himself/herself should be improved.

SUMMARY

Conventionally, attempts to quantify work proficiency degree have been being made. However, for example, when there is a demanded to know a worker working in a bad posture and urge the worker to notice it, a conventional human behavioral-recognition system cannot realize it. Specifically, the system cannot determine the movement of the body of a human and let the target know of a part having a problem.

Therefore, a technique capable of notifying a person who makes a movement, of a part to be improved in the movement of the person is in demand.

One preferable aspect of the present invention relates to a movement evaluation system including: a proficiency degree estimating unit generating a proficiency degree score on the basis of movement data obtained by detecting a movement of a user; an improvement point extracting unit specifying a part of the movement of the user as an improvement point on the basis of the movement data; and an information generating unit generating suggestion information to be presented to the user, on the basis of the improvement point.

In a more concrete example, the system has: a feature extracting unit extracting a plurality of kinds of feature amounts from the movement data; and a storage device storing reference data generated by extracting the plurality of kinds of feature amounts from skilled-person movement data. A feature amount of the movement data and a feature amount of the skilled-person movement data correspond to each other, and the proficiency degree estimating unit notifies the improvement point extracting unit of a period in which the proficiency degree score corresponds to a predetermined condition as a non-proficient period.

In a further concrete example, the improvement point extracting unit compares the feature amount of the movement data with the feature amount of the skilled-person movement data in the non-proficient period and specifies a feature amount which is apart by a predetermined amount or more as the improvement point, and the information generating unit generates the suggestion information on the basis of the feature amount which is apart by the predetermined amount or more.

Another preferable aspect of the present invention relates to a movement evaluation method executed by an information processing device, for a user making a predetermined movement, evaluating the movement, and presenting a problem. The method has: a proficiency degree estimating step of generating a proficiency degree score on the basis of movement data obtained by detecting the movement; a feature amount extracting step of extracting a feature amount from the movement data; an improvement point extracting step of extracting an improvement point of the movement on the basis of the proficiency degree score; and an information generating step of generating work improvement information to be presented to the user, on the basis of the improvement point.

In a further concrete example, a reference feature amount as a feature amount extracted from movement data as a reference is used. In the improvement point extracting step, the reference feature amount and the feature amount of the user are compared with each other to extract the improvement point.

In a further concrete example, a period in which the proficiency degree score deviates from a predetermined range is detected as a non-proficient period. In the improvement point extracting step, data is limited to a range including the non-proficient period, the reference feature amount and the feature amount of the user are compared with each other, and the improvement point is extracted. In such a manner, process load can be lessened.

To a person making a movement, a point to be improved in the movement can be notified.

DETAILED DESCRIPTION

Figure 1:
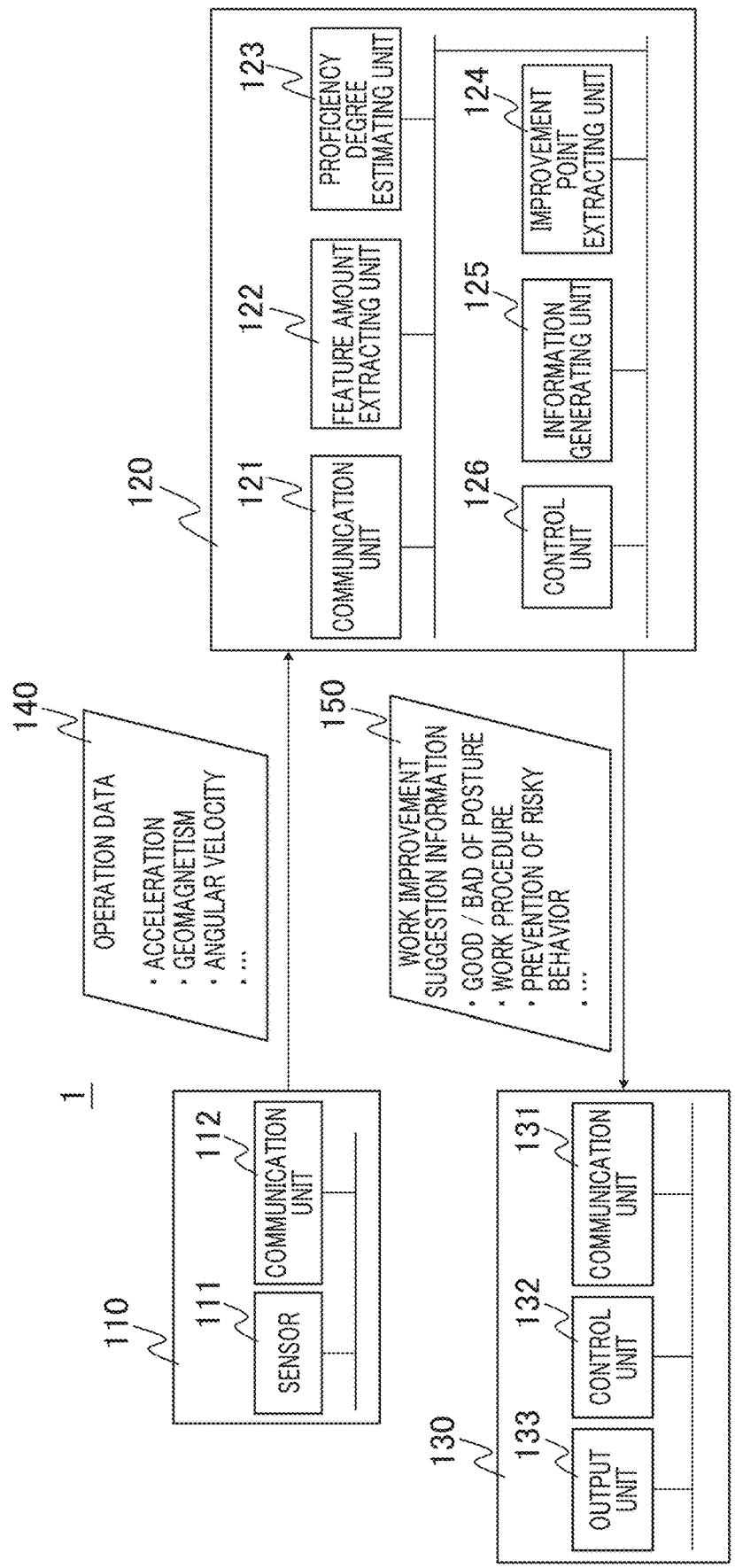
FIG. 1 is a general block diagram of a movement evaluation system of an embodiment.

Embodiments will be described in detail with reference to the drawings. However, the present invention will not be interpreted by being limited to the description of the embodiments described below. It is easily understood by a person skilled in the art that a concrete configuration can be modified without departing from the spirit and scope of the present invention.

In the configurations of the invention described below, the same reference numeral is used for the same parts or parts having similar functions commonly in different drawings, and repetitive description may be omitted.

When there are a plurality of elements having the same or similar functions, in some cases, description will be made by adding different subscripts to the same reference numeral. When it is unnecessary to discriminate a plurality of elements, description may be made without adding subscripts.

Notion such as "first", "second", and "third" in the present specification and the like is attached to identify a component and does not always limit numbers, orders, or contents. Numbers for identifying components are used every context. A number used in one context does not always indicate the same configuration in another context. It does not prevent a component identified by a certain number to serve the same function of a component identified by another number.

The position, size, shape, range, and the like of each configuration in drawings and the like do not always express actual position, size, shape, range, and the like to make understanding of the invention easier. Consequently, the present invention is not always limited to position, size, shape, range, and the like disclosed in drawings and the like.

A component expressed in a singular form in the present specification includes a plural form unless otherwise clearly indicated in context.

To let a person making a movement (hereinbelow, called a user) know a point to be improved in his/her movement, first, the quality of a movement of the user has to be estimated (proficiency degree estimation). Further, a point to be improved in the movement has to be extracted (suggestion of improvement point). In the specification, "movement" denotes a general work in industry, agriculture, and the like and a general movement of the body of a human for a predetermined purpose such as dancing, exercise, playing of instruments, and the like. To concretely specify a point to be improved in a movement, it is desirable to evaluate a movement at a predetermined timing of a specific part in the body of a user.

Such a technique can be used as, for example, a work support system or education system. The work support system can be used for, for example, training of a maintenance work. The education system can be used for, for example, practice of dance or Yoga positions.

First Embodiment

1. System General Configuration

FIG. 1 is a general block diagram of a movement evaluation system of an embodiment. A movement evaluation system 1 includes a sensor unit 110, an information processing device 120, and an information presenting device 130. The sensor unit 110, the information processing device 120, and the information presenting device 130 can communicate with one another via a wired or wireless network (not illustrated).

The sensor unit 110 includes a sensor 111 and a communication unit 112. The sensor 111 is, for example, a wearable sensor which can be attached to the body of the user.

Figure 2:
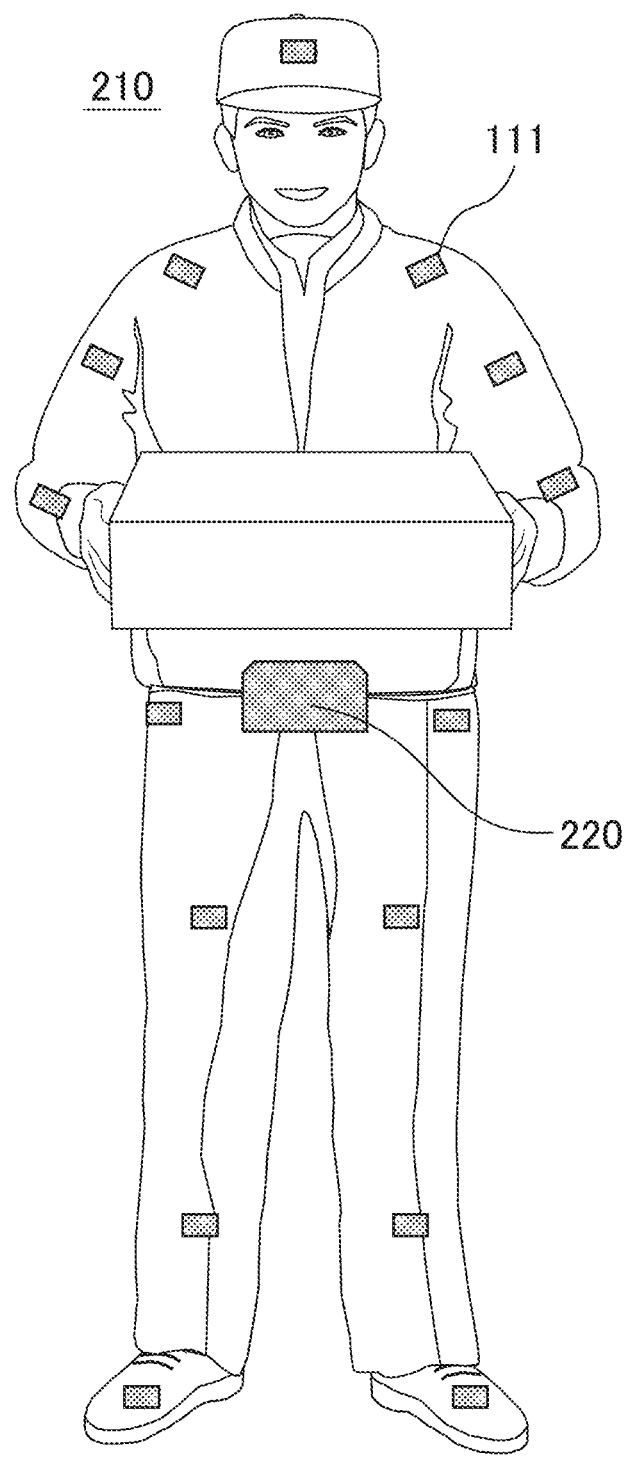
FIG. 2 is a schematic diagram illustrating an example that the user wears sensors.

FIG. 2 is a schematic diagram illustrating an example that a user 210 wears the sensors 111. The sensor 111 is coupled to, for example, a sensor hub 220 directly or via another sensor. The sensor and the sensor hub may be connected by a wire or wirelessly. Movement data 140 sent to the sensor hub 220 is transmitted to the information processing device 120 via the communication unit 112, for example, by radio. The sensor 111 and the sensor hub 220 can supply power by a battery or the like (not illustrated). Arrangement of the sensors 111 in FIG. 2 is an example. The sensors may be attached to parts in the entire body as illustrated in FIG. 2 or only a part of the body such as the upper-part or lower-part of the body in accordance with a movement to be evaluated.

It is sufficient to select one or a plurality of kinds and attachment locations of the sensors 111 in accordance with a movement to be evaluated from known sensors. In the case of directly evaluating a movement of the body of the user 210, a sensor capable of measuring the positions and movements of parts in the body of the user 210 such as an acceleration sensor or a location sensor is desirable. The sensor may be another sensor such as a gyroscope, geomagnetic, video, sound, myoelectric, or angular rate sensor. It is also possible to attach a reflective marker to the user 210, capture an image by a video camera or the like, and measure the position or movement of each of parts of the body. The movement data 140 captured by the sensor 111 is transmitted to the information processing device 120. In the following, an example using an acceleration sensor as a sensor will be described.

The information processing device 120 can be configured by a general server. It is assumed that, as a known hardware configuration of a server, an input device, an output device, a processing device, and a storage device are included. In the embodiment, it is assumed that the functions such as calculation and control are realized when a program stored in the storage device is executed by the processing device to perform a predetermined process in cooperation with another hardware. FIG. 1 illustrates function blocks. In some cases, a program executed by a server or the like, the function of the program, or means realizing the function will be called "function", "means", "part", "unit", "module", or the like.

The above-described configuration may be realized by a single server or another computer in which arbitrary parts of an input device, an output device, a processing device, and a storage device are connected via a network. In the embodiment, a function equivalent to the function configured by software can be also realized by hardware such as FPGA (Field Programmable Gate Array) or ASIC (Application Specific Integrated Circuit). There is a case that a neural network which will be described later is implemented in an FPGA or the like.

The information processing device 120 includes a communication unit 121, a feature amount extracting unit 122, a proficiency degree estimating unit 123, an improvement point extracting unit 124, an information generating unit 125, and a control unit 126.

The communication unit 121 receives the movement data 140 transmitted from the communication unit 112 in the sensor unit 110 and transmits work improvement suggestion information 150 to the information presenting device 130.

The feature amount extracting unit 122 extracts a desired feature amount from the movement data 140. The proficiency degree estimating unit 123 receives the movement data 140 or the feature amount extracted by the feature amount extracting unit 122 as an input and estimates the proficiency degree. In the embodiment, the proficiency degree is estimated on the basis of the movement data 140. The feature amount extracting unit 122 and the proficiency degree estimating unit 123 can be configured by using, for example, a neural network.

The improvement point extracting unit 124 extracts an improvement point by using the feature amount from the feature amount extracting unit 122 and the proficiency degree from the proficiency degree estimating unit 123. The information generating unit 125 generates the work improvement suggestion information 150 for pointing out the improvement point extracted by the improvement point extracting unit 124 to the user 210. The work improvement suggestion information 150 is transmitted from the communication unit 121 to the information presenting device 130. The control unit 126 controls the sequence of the whole operation of the information processing device 120.

The information presenting device 130 is also a kind of an information processing device. For example, a portable information terminal which can be carried by the user 210 can be used but the invention is not limited to it. Although an input device, an output device, a processing device, and a storage device are included as a general hardware configuration, to just notify the user 210 of information, it is sufficient to include a communication unit 131 for receiving information from the information processing device 120, a control unit 132 for the whole, and an output unit 133 displaying information. Alternatively, a device capable of printing information in a paper medium may be provided. The output unit 133 is, for example, a liquid crystal display, a speaker, or a printer.

2. Feature Amount Extracting Unit

Figure 3:
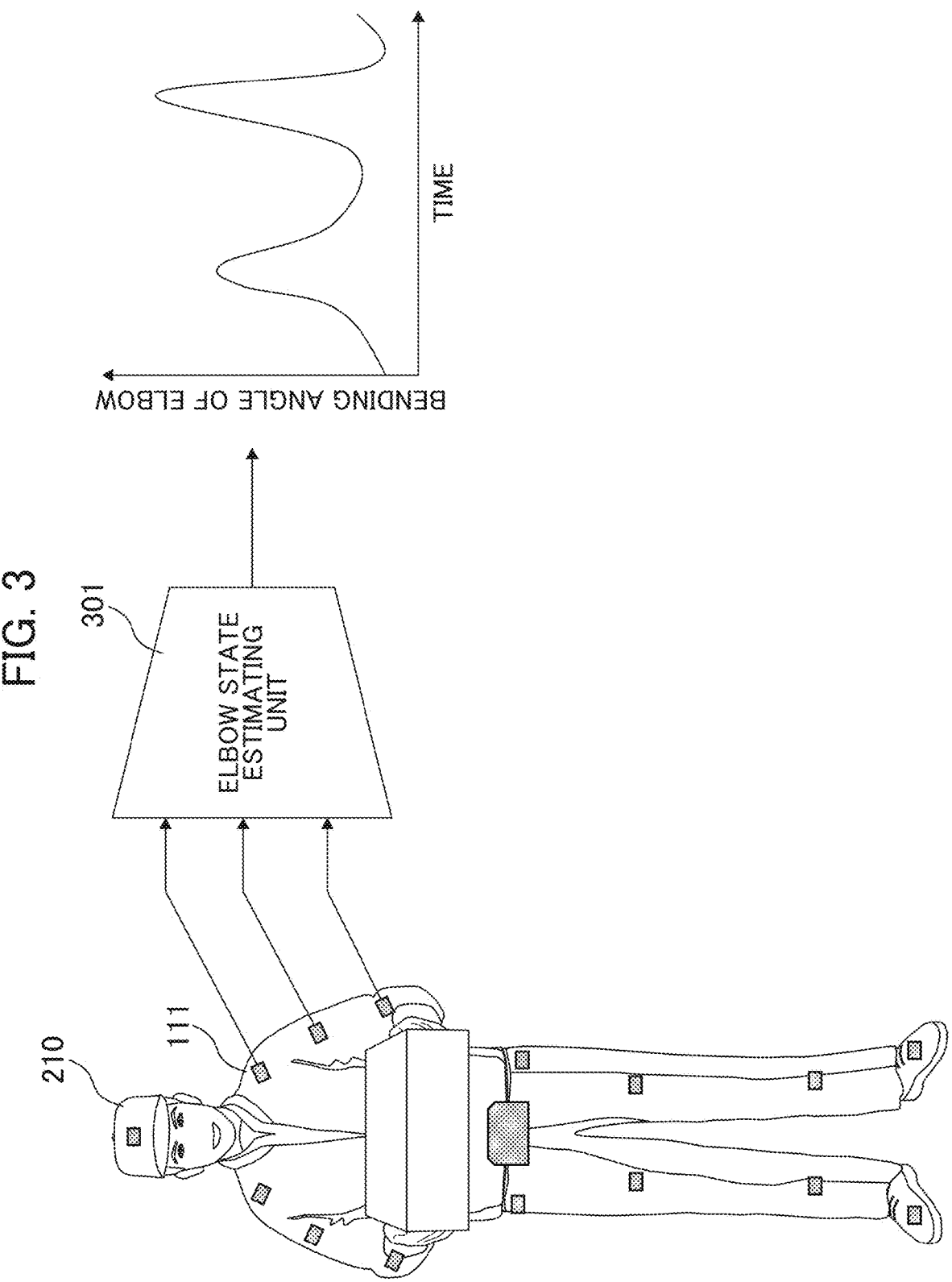
FIG. 3 is a movement conceptual diagram of an elbow state estimating unit.

FIG. 3 is a conceptual diagram for explaining the function of the feature amount extracting unit 122. The feature amount extracting unit 122 extracts a feature amount for evaluating the quality of a movement. One or plural feature amounts is/are defined by the designer of the system or the like in accordance with the purpose of the evaluation of a movement. As the feature amounts, for example, one or plural feature amounts can be arbitrarily defined such as the bending degree of an elbow, the height of the waist, the orientation of the head, or the opening angle of legs. The feature amounts are associated with the features of states of movable parts in the body of the user such as the movements of joints.

To extract a desired feature amount, the sensor 111 obtaining movement data having a necessary physical amount is attached to the user 210. The movement data 140 obtained from arbitrary one or plurality of the sensors 111 is used. In the following, an example of estimating the bending angle of an elbow by using an acceleration sensor will be described.

In FIG. 3, a (left) elbow state estimating unit 301 of the feature amount extracting unit 122 for extracting the bending angle of the elbow from the sensors 111 is illustrated. As illustrated in FIG. 3, the bending angle of the left elbow is estimated from the three sensors 111 attached to the left arm of the user 210 and obtained as time-series data. In the case where a feature amount other than the bending angle of an elbow is desired to be extracted, similarly, it is sufficient to add a waist height extracting unit, a head orientation extracting unit, or the like to the feature amount extracting unit 122. The elbow state estimating unit 301 is constructed by, for example, a deep neural network (DNN) and it is sufficient to perform learning by known supervised learning.

The elbow state estimating unit 301 can perform estimation not by a DNN but also by regular calculation using acceleration data of the sensors 111. In the case of estimating the bending angle of an elbow from acceleration, the initial state of the user 210 is obtained and used. For this purpose, preliminarily, the user 210 is made in predetermined postures (such as standing posture), and detection of the positions of the sensors 111 and the like is performed. Alternatively, as the sensors 111, position sensors may be used in place of the acceleration sensors. In such a manner, the kind of the sensor can be freely selected in accordance with a feature amount desired to be estimated.

At the time of operation of the system, the extracted feature amounts are stored as time-series data by kinds in the storage device.

3. Proficiency Degree Estimating Unit

The proficiency degree estimating unit 123 receives the movement data 140 from the sensors 111 and estimates the proficiency degree. The proficiency degree estimating unit 123 can be configured by using a neural network educated by supervised learning.

Figure 4:
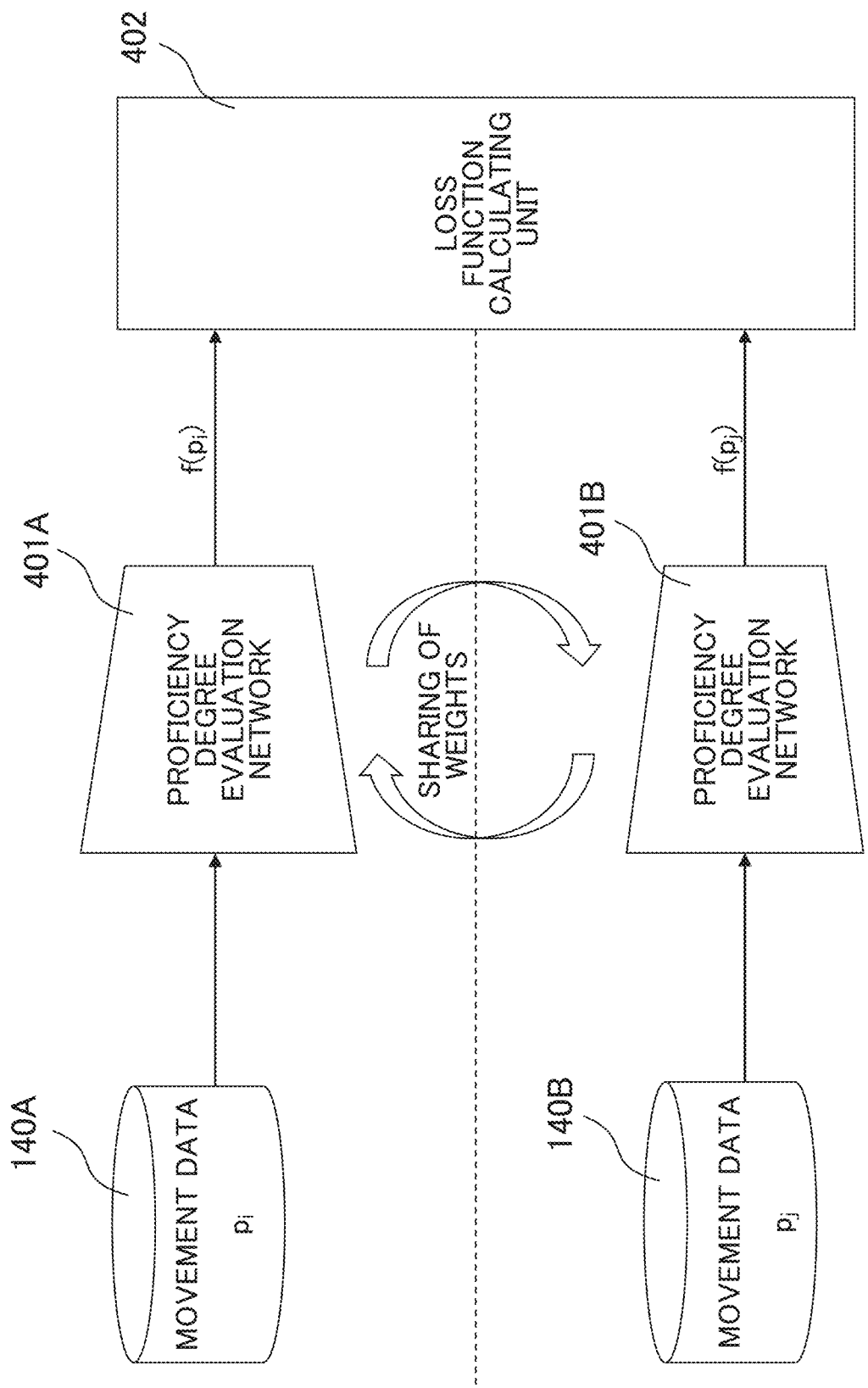
FIG. 4 is a block diagram for explaining learning of a proficiency degree evaluation network of a first embodiment.

FIG. 4 is a block diagram for explaining learning of a proficiency degree evaluation network 401 as a component of the proficiency degree estimating unit 123. In the example, the proficiency degree evaluation network 401 is learned by using a Siamese network. As illustrated in the diagram, two pieces of movement data 140A and 140B (values are set as $p_i$, $p_j$) are input to proficiency degree evaluation networks 401A and 401B, and proficiency degree scores $f(p_i)$ and $f(p_j)$ of the movement data are calculated. The Siamese network is a technique using the deep neural network (DNN), and two DNNs commonly use weights. The two pieces of movement data $p_i$ and $p_j$ are input separately to the proficiency degree evaluation networks 401 as the same DNNs and two proficiency degree scores $f(p_i)$ and $f(p_j)$ are obtained. From the scores, a loss function is calculated by a loss function calculating unit 402. As the loss function, a function whose value decreases as the score on a skilled person side becomes larger when movement data of a skilled person and an unskilled person is input is selected.

Figure 5:
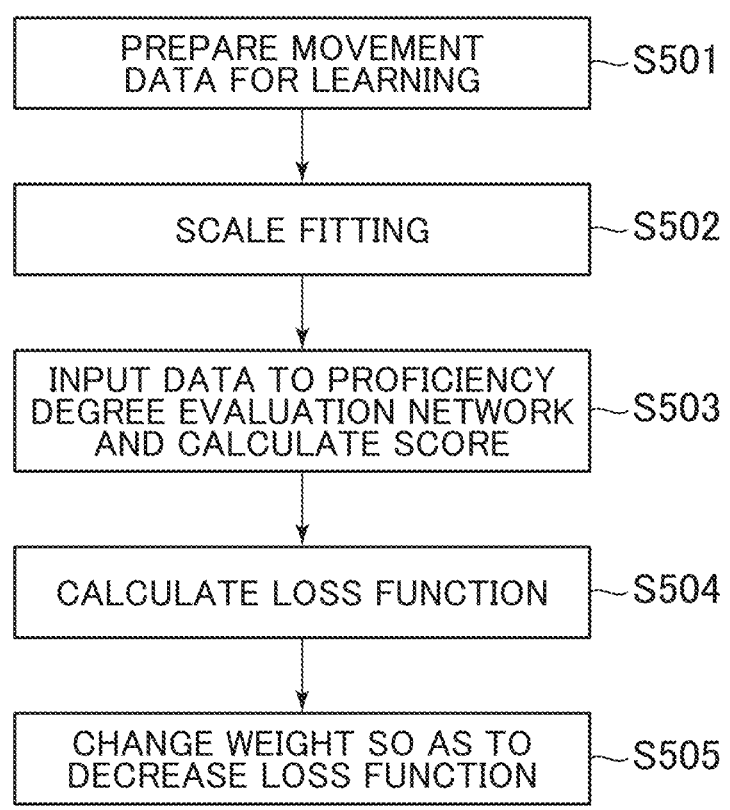
FIG. 5 is a flowchart explaining learning steps of the proficiency degree estimating unit.

FIG. 5 is a flowchart explaining learning steps of the proficiency degree estimating unit 123. First, movement data for learning to learn a DNN is prepared and stored in, for example, a storage device (S501). The movement data for learning is movement data obtained from the movements of a skilled user and an unskilled user. To each of the movement data for learning, information defining superiority/inferiority of the proficiency degree among the movement data, such as a proficiency degree evaluation score obtained by, for example, observing a movement by a skilled person is attached.

To match physical constitutions or movement speeds of persons who make movements, scale fitting of movement data is performed (S502). For example, 170 cm of height is set as a reference, and the sizes of parts of the body of the user are increased or decreased. Also with respect to the movement speed, the time axis of the movement data is increased or decreased using predetermined length as a reference. For example, when performance of a series of movements to lift a thing in 60 seconds is set as a reference, the time axis of movement of data of a user performing the series in 120 seconds is compressed to the half. In the case of implement the DNN in a long short-term memory (LSTM), it is not always necessary to perform normalization or the like in the time direction. Also with respect to the sizes of the bodies, if there is a large amount of data, a network can be made learn also variations of bodies. By preliminarily obtaining movement data from users having similar physical constitutions and arranging movement times at the time of obtaining the movement data, the scale fitting S502 can be omitted. As it is considered that an effect equivalent to that of the scale fitting can be obtained by a DNN depending on the configuration of the DNN, the scale fitting S502 can be omitted.

The movement data for learning in which evaluation scores of the proficiency degrees are known is input to the proficiency degree evaluation networks 401A and 401B, and a score is calculated (S503). A loss function is calculated from the proficiency degree scores of the proficiency degree evaluation networks 401A and 401B (S504).

Formula 1 indicates an example of a method of calculating loss function $L_{total}$.

$$L_{total} = L_{rank} + L_{sim} \quad (1)$$

$$L_{rank} = \sum_{k=1}^{N} \max(0, m - f(p_i) + f(p_j))$$

(When $p_i$ is better than $p_j$)

$$L_{sim} = \sum_{k=1}^{M} \max(0, |f(p_i) - f(p_j)| - m')$$

(When $p_i$ has similar skill level to $p_j$)

where $N$, $M$ is a total number of pairs

In the example of the learning, it is a precondition that proficient movement data obtained from a proficient movement and non-proficient movement data obtained from a non-proficient movement are discriminated from each other. The discrimination can be determined from the difference of evaluation scores of the proficiency degrees. A loss function (error) is calculated according to the following rule, and learning is performed so as to decrease the loss function.

In the case where there is superiority/inferiority in the two pieces of movement data inputted (for example, in the case where the difference between evaluation scores of the proficiency degrees is equal to or larger than a predetermined threshold), when the score of the superior movement data is lower than that of the inferior movement data, the difference is set as an error. When it is desired to widen the difference between the scores to a predetermined value or larger, m in Formula 1 is increased. In the case where there is no superiority/inferiority in two pieces of movement data (for example, when the difference between evaluation scores of the proficiency degrees is less than a predetermined threshold, so-called equivalent levels), when the difference of the scores is calculated and the calculated difference is equal to or larger than a predetermined value (m'), the amount exceeding the predetermined value is set as an error. The two errors are added and learning is performed.

In two pieces of movement data having superiority/inferiority as described above, the difference of the scores is used as an error and DNN is learned so that the difference between the scores increases. In equivalent data, the difference of the scores is used as an error and DNN is learned so that the difference between the scores decreases. It is sufficient to perform learning by one or a combination of the both methods. In the example of Formula 1, both of the methods are combined. At the time of calculating the loss function $L_{total}$, $L_{rank}$ and $L_{sim}$ are calculated according to known priority/superiority of movement data which is input, and total of them becomes $L_{total}$.

As the proficiency degree evaluation network 401, a model selected according to a movement to be evaluated and a viewpoint of evaluation is learned and prepared. The proficiency degree evaluation network 401 generated by the above-described learning method is implemented in the proficiency degree estimating unit 123. The proficiency degree evaluation network which is implemented may be one of the proficiency degree evaluation networks 401A and 401B.

In the embodiment, the proficiency degree evaluation network 401 is implemented in the LSTM. When a series of work time-series sensor data is input every time unit, a score at each time is output. For example, with respect to acceleration data of a work of 60 seconds, data of one second each is input to the proficiency degree evaluation network 401. At the time of learning, using an average of the scores at times as $f(p_i)$, an error is calculated. On the other hand, at the time of inference after implementation to the movement evaluation system 1, the proficiency degree score of every predetermined time (for example, every second) is output in chronological order.

4. Output of Proficiency Degree Estimating Unit

Figure 6:
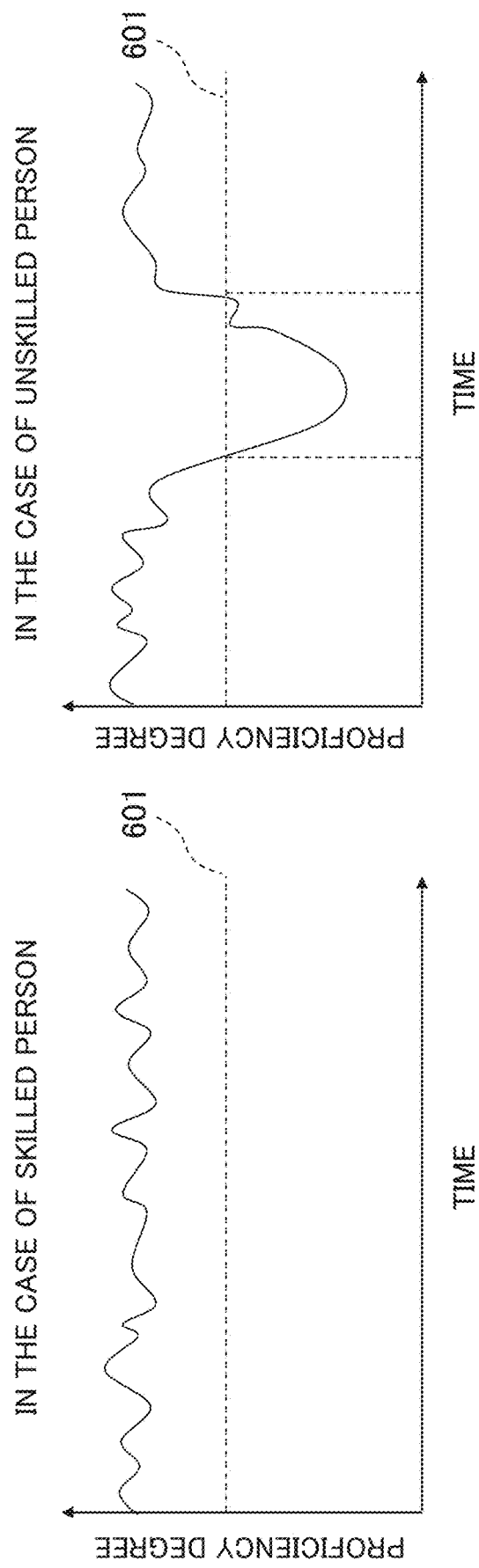
FIG. 6 is a graph comparison diagram of a proficiency degree score of a skilled person and a proficiency degree score of an unskilled person.

FIG. 6 illustrates comparison between a proficiency degree score of a skilled person and a proficiency degree score of an unskilled person. Since the proficiency degree scores are time-series data, the horizontal axis indicates time, and the vertical axis indicates proficiency degree score. In the example, in the proficiency degree score of an unskilled person, a region that the proficiency degree decreases exists in a certain time zone. For example, when the proficiency degree score becomes below predetermined threshold 601 for predetermined time or longer, the proficiency degree estimating unit 123 recognizes that the non-proficient operation is performed. The method of detecting the non-proficient movement may be another method obtaining an equivalent effect. For example, without using a threshold, non-proficient movement may be determined on the basis of relative fluctuations of the proficiency degree score. The threshold 601 may not a fixed threshold but may fluctuate.

When the proficiency degree estimating unit 123 recognizes a non-proficient movement, it notifies the improvement point extracting unit 124 of a time zone corresponding to the non-proficient movement. The improvement point extracting unit 124 obtains feature amount data including the corresponding time zone from the feature amount extracting unit 122 and refers to it. It compares the obtained data with transition of feature amount data of a skilled person which is preliminarily stored and specifies a feature amount of a large difference. At the time of operation of the system, estimated proficiency degree scores are stored as time-series data in the storage device.

In the embodiment, by preparing movement data and superiority/inferiority information of the proficiency degree of each worker in advance by the learning method using a neural network, a system estimating the proficiency degree of a movement in a real-time manner can be realized. By using the estimated proficiency degree, a correct movement can be suggested at the time of education for learning work or a work (body posture) of high load can be prevented at the time of an actual work.

5. Improvement Point Extracting Unit

Figure 7:
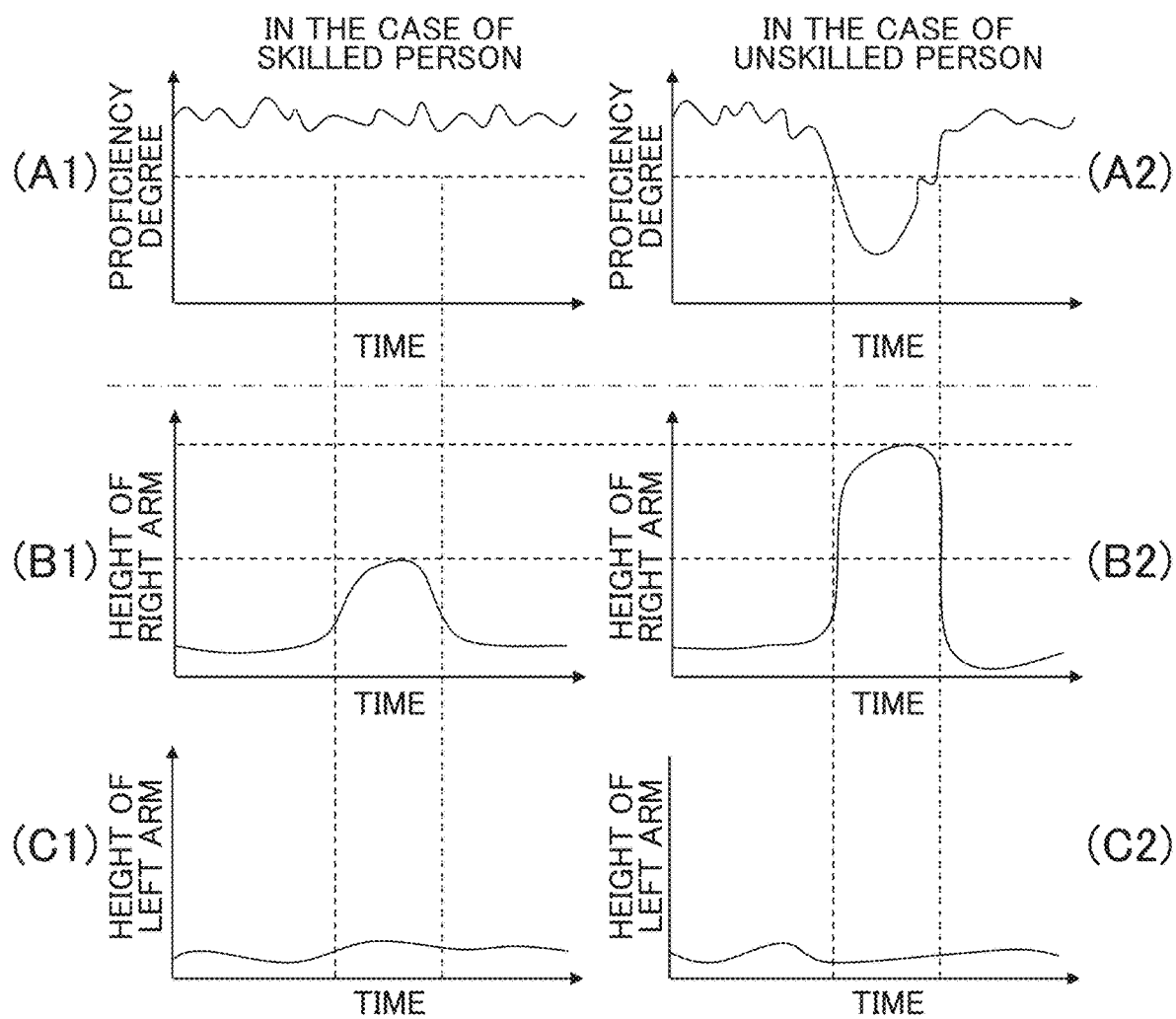
FIG. 7 is a diagram of graphs of the proficiency degree and characteristic feature amount for explaining examples of movements of an improvement point extracting unit.

FIG. 7 illustrates an example of the operation of the improvement point extracting unit 124. In FIG. 7, (A1) indicates a proficiency degree score of a skilled person as a reference. (B1) indicates height of the right arm as one of the feature amounts of the skilled person. (C1) indicates height of the left arm as one of the feature amounts of the skilled person. Similarly, (A2) indicates a proficiency degree score of a user. (B2) indicates height of the right arm as one of the feature amounts of the user as an unskilled person. (C2) indicates height of the left arm as one of the feature amounts of the user. In the feature amount "height of the right arm", the difference can be recognized between the feature amount of the skilled person and that of the user. It can be executed by detecting the difference between them by a predetermined threshold or larger. On the other hand, no difference can be seen between them in the feature amount "the height of the left arm". Therefore, it is understood that the point to be presented as an improvement point to the user by the system is "height of the right arm" in a time zone corresponding to the non-proficient movement. In such a manner, the improvement point extracting unit 124 extracts the movement of a part in the entire movement of the body of the user as a movement to be improved.

The improvement point extracting unit 124 which performed the above analysis transmits a feature amount to be improved, a timing to be improved, the difference from a skilled person, and the like to the information generating unit 125. The information generating unit 125 generates the work improvement suggestion information 150 to be presented to the user on the basis of the information received, graphic data stored in advance, or the like. The work improvement suggestion information 150 is transmitted from the communication unit 121 to the information presenting device 130.

6. Information Presenting Device

Figure 8:
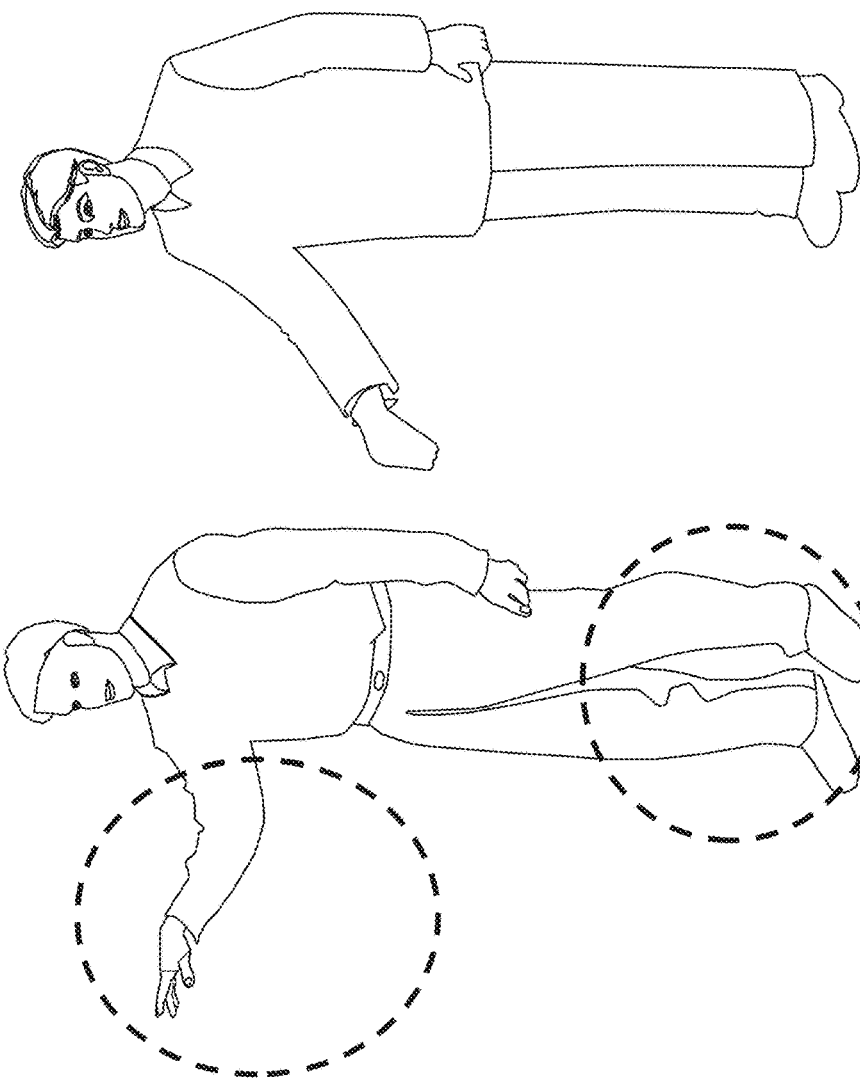
FIG. 8 is a conceptual diagram for explaining information displayed in an output unit of an information presenting device.

FIG. 8 is a conceptual diagram for explaining information displayed in a liquid crystal display as an example of the output unit 133 of the information presenting device 130. To facilitate understanding of the user, a feature amount to be improved is displayed by using a model of a human shape. The presentation may be performed by comparison by arranging the model of a skilled person and that of the user side by side or superimposing them. In the example of FIG. 8, on the basis of the information from the improvement point extracting unit 124, improvements with respect to the position of the right arm and the opening angle of the legs are presented by computer graphics (CG). To facilitate understanding of the user, text characters or sound may be output. A text generating method can be performed by captioning using machine learning or display using a prepared pattern. A timing in the whole movement, of a time zone corresponding to the non-proficient movement may be also displayed. It is more effective to use a moving picture CG at this time.

7. Movement Evaluation and Improvement Suggestion Sequence

Figure 9:
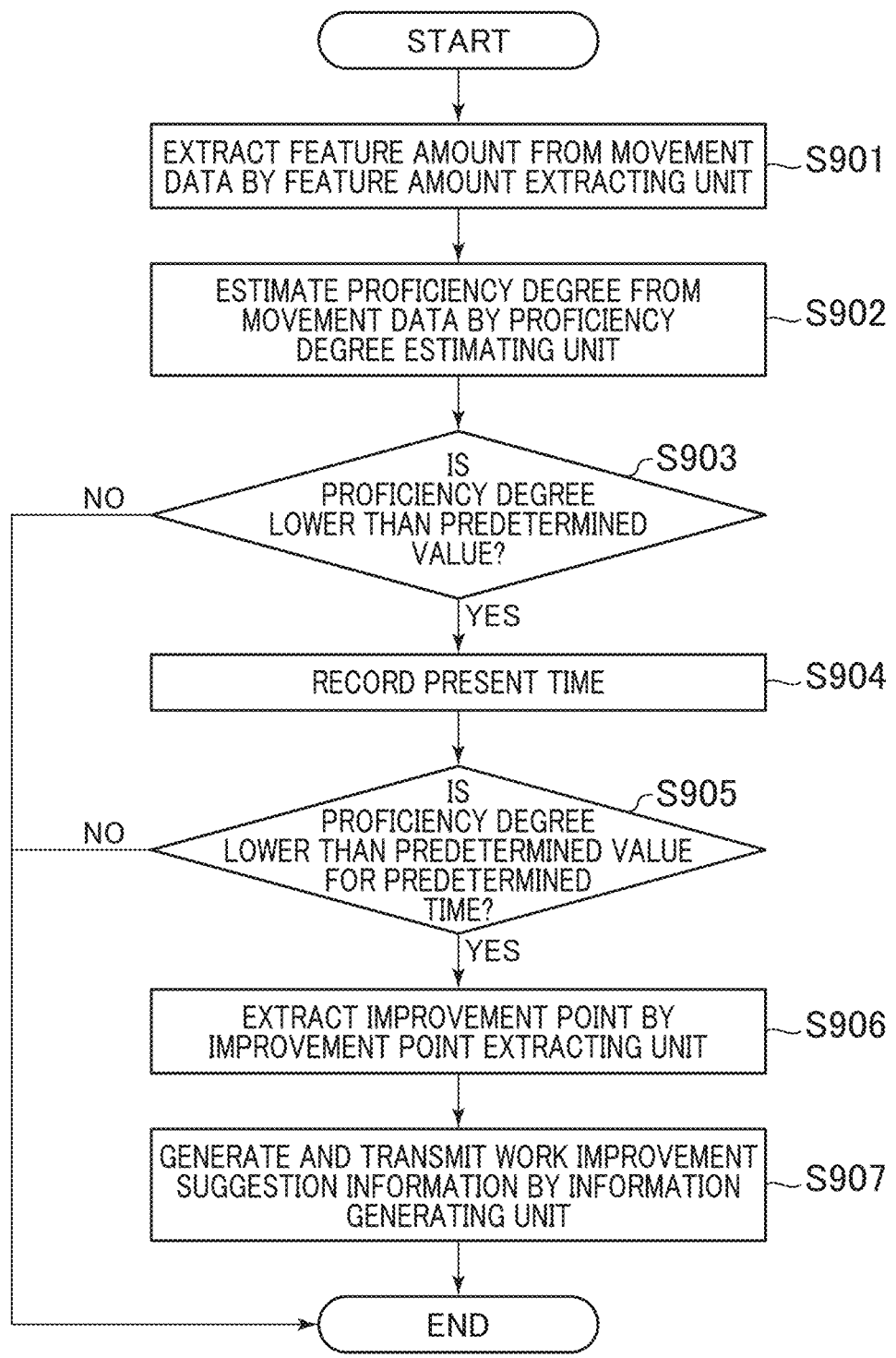
FIG. 9 is a flowchart explaining a movement evaluation and improvement suggestion sequence by an information processing device.

FIG. 9 is a flowchart explaining a movement evaluation and improvement suggestion sequence by the information processing device 120 in FIG. 1. In process S901, the feature amount extracting unit 122 extracts a desired feature amount (usually a plurality of kinds) from the movement data 140 received by the communication unit 121. In process S902, the proficiency degree estimating unit 123 estimates a proficiency degree score from the movement data 140. The feature amount and the proficiency degree score are time-series data.

In process S903, the proficiency degree estimating unit 123 detects whether the proficiency degree score becomes lower than a predetermined threshold or not. In process S904, time when the proficiency degree score becomes lower than the predetermined threshold is recorded. In process S905, the proficiency degree estimating unit 123 determines whether the proficiency degree score is below the threshold for a predetermined period or not. The determination result is sent with the period in which the proficiency degree score becomes below the threshold (in the following, called the non-proficient period) and, as necessary, data of the proficiency degree score including the non-proficient period to the improvement point extracting unit 124. In process S906, the improvement point extracting unit 124 extracts an improvement point of movement.

Figure 10:
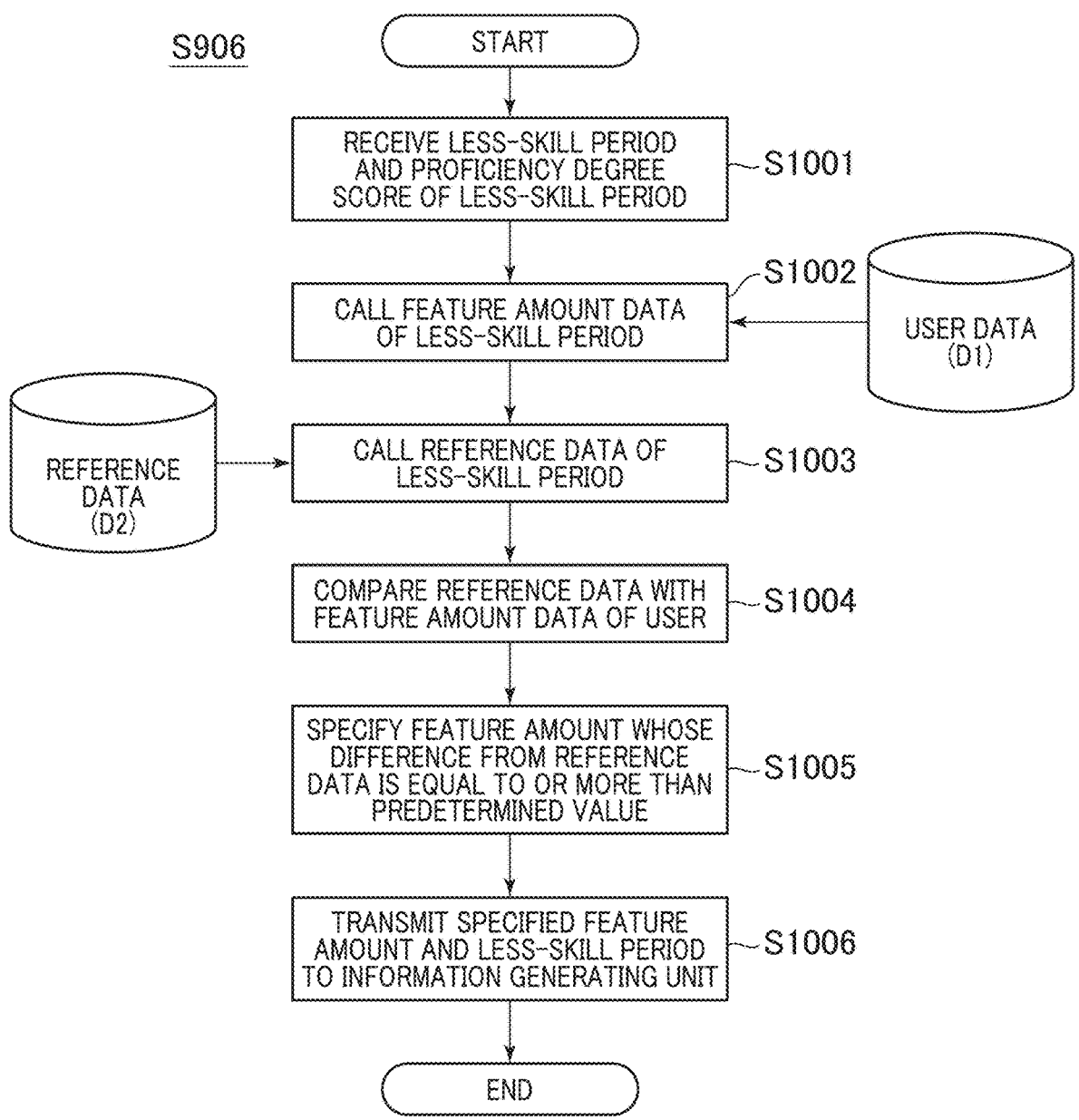
FIG. 10 is a flowchart illustrating the details of processes of the improvement point extracting unit.

FIG. 10 is a flowchart illustrating the details of the process S906 of the improvement point extracting unit 124. In process S1001, the improvement point extracting unit 124 receives information of the non-proficient period (for example, the beginning and termination using the movement start as the origin point) from the proficiency degree estimating unit 123. As necessary, it also receives the proficiency degree score including the non-proficient period.

In process S1002, the improvement point extracting unit 124 calls data of a feature amount including the non-proficient period from user data D1 recorded. When there are a plurality of kinds of feature amounts, all of them are called. By limiting to the data in the non-proficient period, the process amount after that can be compressed.

The user data D1 is time-series data of the feature amount of the user 210 extracted by the feature amount extracting unit 122 on the basis of the movement data 140 transmitted from the sensor unit 110. The time-series data of the proficiency degree score of the user 210 estimated by the proficiency degree estimating unit 123 may be also included. Basically, data in the entire period in which the user makes movements is stored. As those data, data preliminarily obtained in the entire period in which the user makes movements in another place or occasion and stored in the storage device may be used.

In process S1003, data of a feature amount including the non-proficient period is called from reference data D2. The reference data D2 is feature amount data of a skilled person, which is, for example, generated in advance from movement data of the user whose proficiency degree score is equal to or higher than a predetermined score and stored in the storage device. The reference data D2 may include a proficiency degree score estimated by the proficiency degree estimating unit 123. The movement, the movement period, and the feature amount of the reference data D2 have to be matched to those of the user data D1. For convenience of explanation, it is assumed that the above-described scale fitting is performed on the user data and the reference data.

In process S1004, the non-proficient period of the feature amount of the user data and that the feature amount of the reference data are compared every same feature amount.

In process S1005, as illustrated in FIG. 7, in the non-proficient period, the feature amount of the user data apart from the feature amount of the reference data by the predetermined amount or more is specified. The movement related to the specified feature amount is an object to be improved.

In process S1006, the specified feature amount and the non-proficient period are transmitted to the information generating unit 125.

Figure 11:
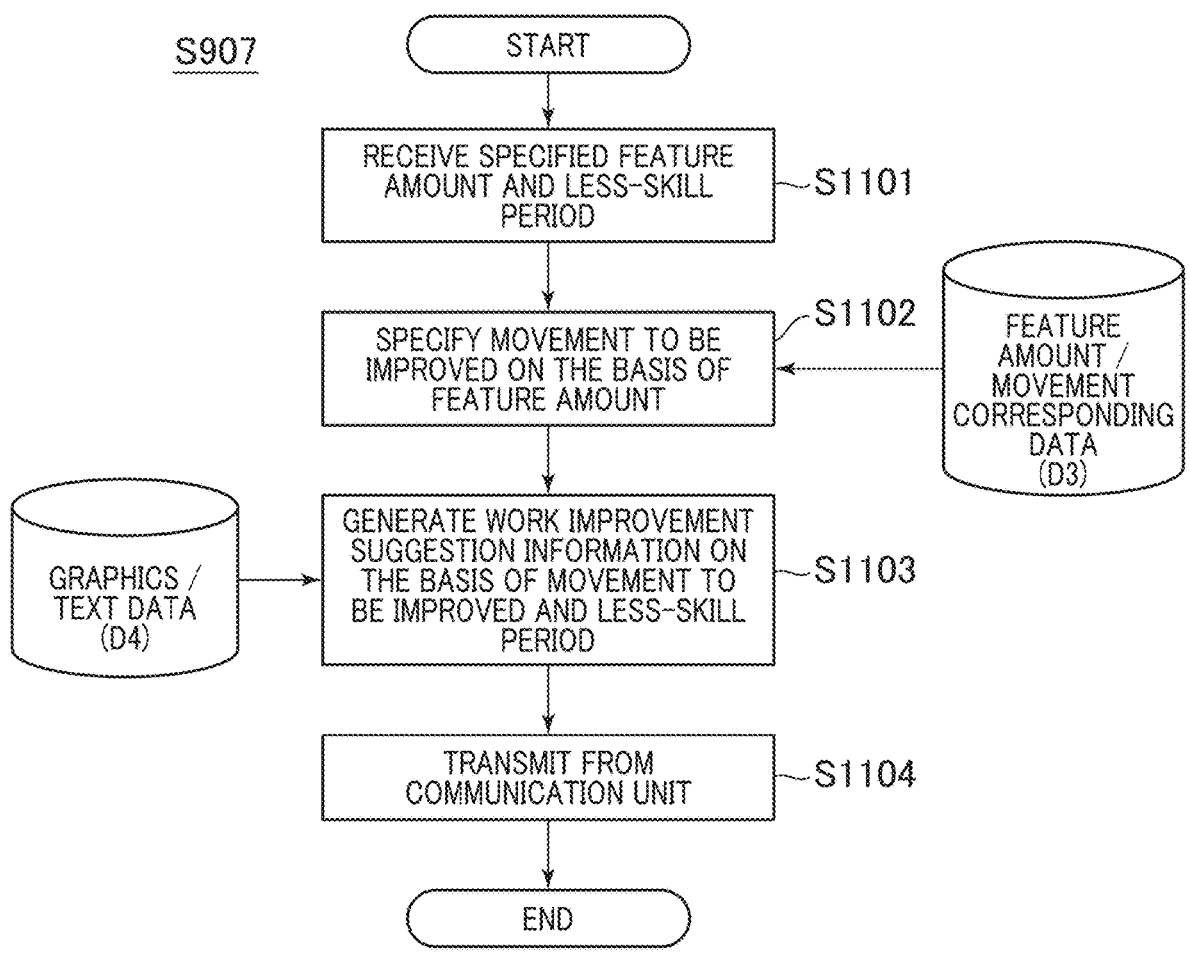
FIG. 11 is a flowchart illustrating the details of processes of an information processing unit.

FIG. 11 is a flowchart illustrating the details of the process S907 of the information processing unit 125. In process S1100, the feature amount specified from the improvement point extracting unit 124 and the non-proficient period are received.

In process S1102, a corresponding movement is specified from the specified feature amount. At this time, for example, feature amount/movement corresponding data D3 in which each feature amount and a movement are associated is referred to. The feature amount/movement corresponding data D3 is a database preliminarily generated and stored by a designer or the like of a system, and the feature amount and a movement related to it are associated. For example, the movement "movement of the right arm" is associated with the feature amount "height of the right hand". It is assumed that such associated data is also defined by the designer or the like of the system and stored in the storage device in advance.

In process S1103, the work improvement suggestion information 150 is generated based on the movement to be improved and the non-proficient period. At this time, for example, using graphics/text data D4 prepared in advance, an image reproducing and displaying "movement of the right arm" in the non-proficient period and information displaying a comment for improvement are generated (refer to FIG. 8). In process S1104, the work improvement suggestion information 150 is transmitted to the information presenting device 130 and presented to the user 210.

8. Effects of Embodiment

According to the embodiment described above, the system of estimating the quality of a movement of a person making movements, extracting a problem of a timing in the movement in the part, and suggesting improvement to the user can be provided.

Particularly, not finding a problem for a check point prepared in advance, a part having a problem can be flexibly specified on the proficiency degree score base which is output, and a part having a problem in a movement of a work can be automatically extracted. For example, a problem in "a bending posture" in "a lifting movement", a problem in "the way of bending of the waist or knee", or the like can be specified by properly setting a feature amount.

In the work improvement suggestion information 150, an improvement point can be suggested on the basis of the movement of a skilled person to the movement having a problem. For example, the bending posture of the skilled person and that of a worker can be displayed side by side or a part of different movements of the part in the body can be emphasized.

Second Embodiment

The first embodiment relates to the case that proficient movement data and non-proficient movement data is obtained as movement data for learning. Next, a learning method of a proficiency degree evaluation network in the case where only proficient movement data is obtained will be described. In a second embodiment, only work data of a skilled person is used and, by combining efficient compression of work data information and an abnormality detection algorithm, the proficiency degree of a worker is estimated.

Figure 12:
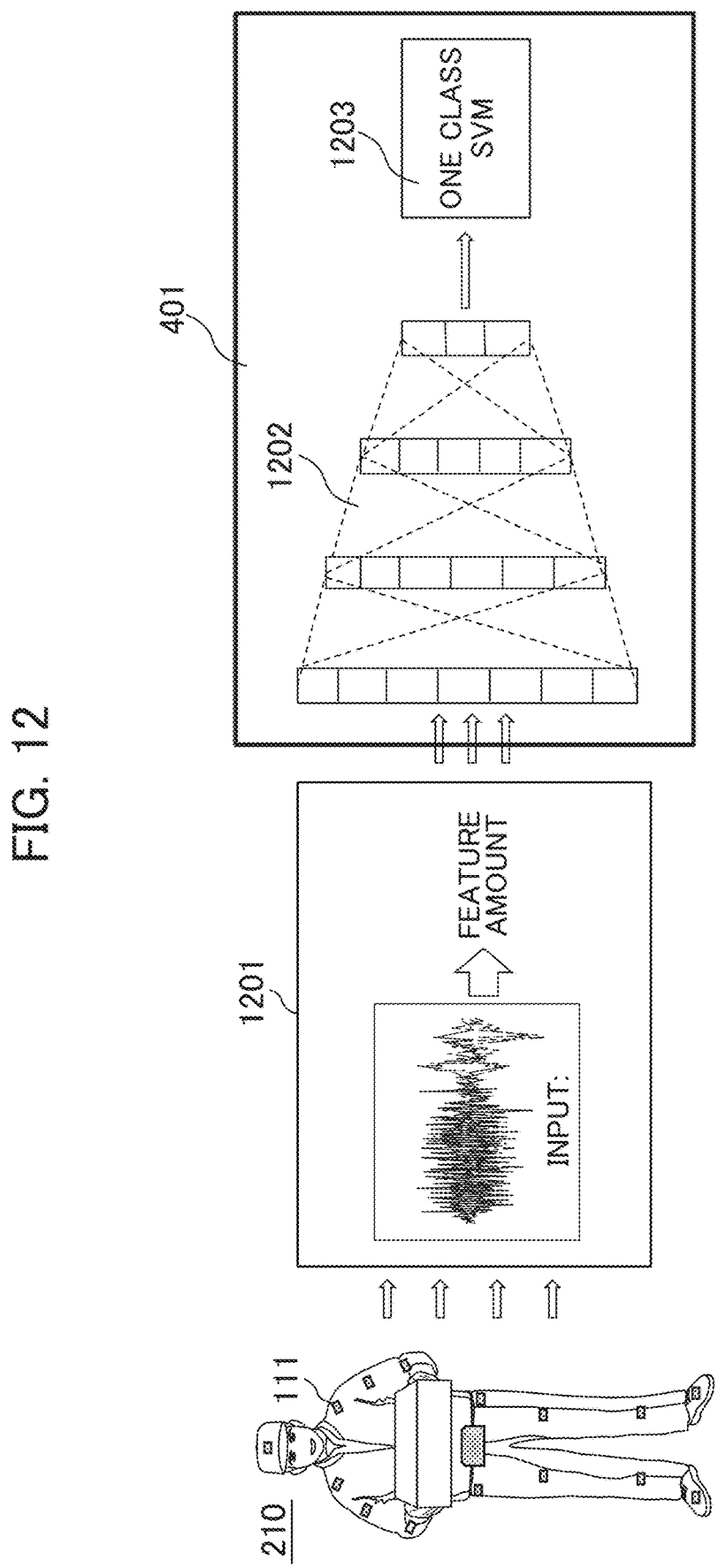
FIG. 12 is a block diagram explaining learning of a proficiency degree evaluation network of a second embodiment.

FIG. 12 is a block diagram explaining learning of the proficiency degree evaluation network 401 as a component of the proficiency degree estimating unit 123. In this example, movement data used is only movement data obtained from the sensors 111 attached to the user 210 as a skilled person. A feature amount extracting unit 1201 is similar to the feature amount extracting unit 122 in FIG. 1 and extracts various feature amounts (for example, transition of the angle of each joint) from movement data. An autoencoder 1202 is a neural network performing compression of a dimension by unsupervised learning using only input data as known for the purpose of extracting a feature of data.

In the embodiment, a feature amount is used as input and a dimension can be compressed by using the autoencoder 1202. The compressed feature amount is input to a support vector machine (SVM) 1203 of 1 class. As it is known, the 1-class SVM 1203 identifies an outlier on assumption that input values belong to a single class and other values are outliers. In the example, the single class is data of a skilled person, and outliers are data of an unskilled person. The proficiency degree evaluation network 401 generated by the learning method described above is implemented in the proficiency degree estimating unit 123.

Figure 13:
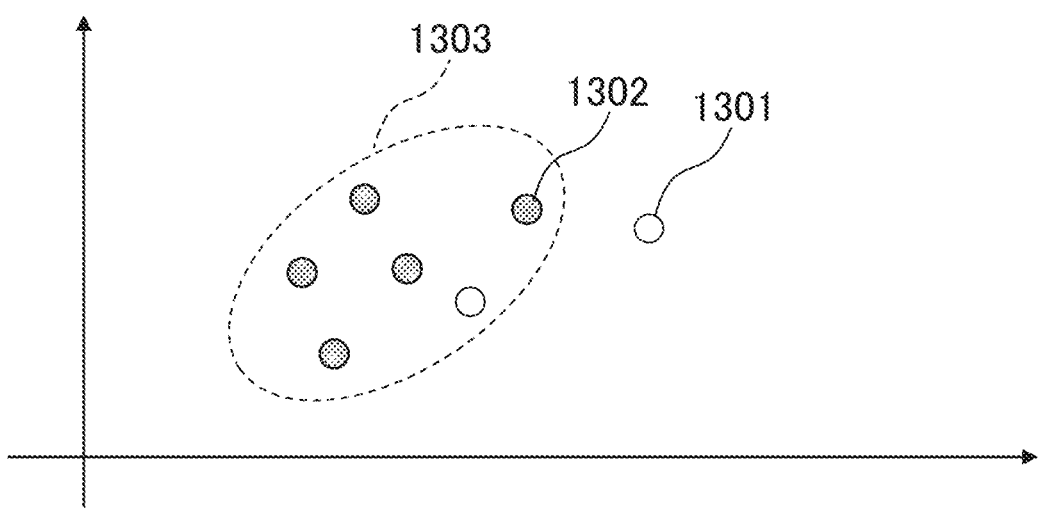
FIG. 13 is a conceptual diagram explaining operation of a 1-class SVM.

FIG. 13 is a conceptual diagram explaining operation of the 1-class SVM 1203 implemented in the proficiency degree estimating unit 123. At the time of inference after implementation in the movement evaluation system 1, in a manner similar to that at the time of learning, a feature amount is compressed, resultant data is input as compressed data 1301 to be evaluated, and the proficiency of the skilled person of the compressed data 1301 is estimated as a score on the basis of the distance to a border 1303 of a region in which compressed skilled person data 1302 exists. At the time of learning, a series of time-series sensor data is divided every time unit, and the resultant data is learned as input data. Also at the time of inference, by inputting the data every time unit, a score is obtained in a real-time manner.

The proficiency degree estimating unit 123 in which the proficiency degree evaluation network 401 learned as described above is implemented outputs a proficiency degree score in a real-time manner on the basis of movement data which is input on a predetermined time unit basis.

The configurations and operations of parts other than the above may be similar to those of the first embodiment. However, since an input at the time of learning of the proficiency degree evaluation network 401 is a feature amount (as a rule, all in the case where there are a plurality of feature amounts), an input of the proficiency degree estimating unit 123 at the time of implementation is a feature amount extracted by the feature amount extracting unit 122.

Third Embodiment

In the first and second embodiments, a movement to be improved is specified on the basis of a feature amount. As another example, without using a feature amount by the feature amount extracting unit 122, by analyzing the activity degree of the neural network of the proficiency degree estimating unit 123 by the improvement point extracting unit 124, an input which exerts large influence on the proficiency degree score is specified and, a movement to be improved can be specified on the basis of the specified input.

In this case, the feature amount extracting unit 122 of the information processing device 120 in FIG. 1 is omitted, and an input of the proficiency degree estimating unit 123 is the movement data 140.

Fourth Embodiment

In the first to third embodiments, an improvement point can be pointed out almost in a real-time manner for the movements of the user 210. However, the work improvement suggestion information 150 is not always presented immediately. For example, when the movement of the user accompanies danger, it is desirable to notify the user 210 immediately.

Consequently, it can be also configured that whether a feature amount or a proficiency degree score deviates from an allowable value is determined in a real-time manner in the improvement extracting unit 124 or the like and, in the case of deviation, an alarm is immediately generated to the user 210. On the other hand, improvement which is not urgent can be notified at a preset timing such as a timing at the end of a work or after the end of business.

What is claimed is:

1. A movement evaluation system comprising:
   a storage device storing thereon a program; and
   a processor executing instructions contained in the program to cause the movement evaluation system to perform the steps of:
   generating a proficiency degree score based on movement data obtained by detecting a movement of a user;
   specifying a part of the movement of the user as an improvement point based on the movement data;
   generating suggestion information to be presented to the user, based on the improvement point; and
   extracting a plurality of kinds of feature amounts from the movement data,
   wherein the storage device stores reference data generated by extracting the plurality of kinds of feature amounts from skilled-person movement data,
   wherein a feature amount of the movement data and a feature amount of the skilled-person movement data correspond to each other,
   wherein the processor further causes the movement evaluation system to further perform the steps of:
   notifying of a period in which the proficiency degree score corresponds to a predetermined condition as a non-proficient period,
   comparing the feature amount of the movement data with the feature amount of the skilled-person movement data in the non-proficient period and specifying a feature amount which is apart by a predetermined amount or more as the improvement point, and
   generating the suggestion information based on the feature amount.

2. The movement evaluation system according to claim 1, wherein the processor further causes the movement evaluation system to further perform the step of:
   information generating unit generates the suggestion information based on the feature amount which is apart by the predetermined amount or more and the non-proficient period.

3. The movement evaluation system according to claim 1, wherein the movement data of the user and the skilled-person movement data are subjected to scale fitting to fit at least one of physique difference and movement speed of a person who makes movements.

4. The movement evaluation system according to claim 1, further comprising a proficiency degree evaluation network constructed by a convolution network using the movement data as an input and using the proficiency degree score as an output.

5. The movement evaluation system according to claim 1, further comprising a proficiency degree evaluation network using the feature amount as an input and using the proficiency degree score as an output and constructed by an autoencoder and a 1-class support vector machine.

6. The movement evaluation system according to claim 1, wherein the feature amount is associated with a state of a movable part in a body of the user.

7. A movement evaluation method executed by an information processing device, for a user performing a movement, evaluating the movement, and presenting a information, comprising:
   a proficiency degree estimating step of generating a proficiency degree score based on movement data obtained by detecting the movement;
   a feature amount extracting step of extracting a feature amount from the movement data;
   an improvement point extracting step of extracting an improvement point of the movement based on the proficiency degree score; and
   an information generating step of generating work improvement information to be presented to the user, based on the improvement point;
   wherein a reference feature amount as a feature amount extracted from movement data as a reference is used, and
   wherein, in the improvement point extracting step, the reference feature amount and the feature amount of the user are compared with each other to extract the improvement point,
   wherein a period in which the proficiency degree score deviates from a predetermined range is detected as a non-proficient period, and
   wherein, in the improvement point extracting step, data is limited to a range including the non-proficient period, the reference feature amount and the feature amount of the user are compared with each other, and the improvement point is extracted.

8. The movement evaluation method according to claim 7, wherein the feature amount is a feature of a movement of each of joints of a body of the user.

9. The movement evaluation method according to claim 7, wherein the movement data is obtained by a sensor which can be attached to the user.

10. The movement evaluation method according to claim 7, wherein the proficiency degree score is generated from the movement data or the feature amount extracted from the movement data.

11. The movement evaluation method according to claim 7, wherein when at least one of the proficiency degree score and the feature amount deviates from a predetermined range, an alarm is generated immediately to the user.

* * * * *